United States Patent [19]

Galbo

[11] Patent Number: 5,374,729
[45] Date of Patent: Dec. 20, 1994

[54] PROCESS FOR PREPARING N-METHOXY DERIVATIVES OF 4-HYDROXY-2,2,6,6-TETRAMETHYL-PIPERIDINE AND 2,2,6,6-TETRAMETHYL-4-PIPERIDONE

[75] Inventor: James P. Galbo, Wingdale, N.Y.

[73] Assignee: Ciba-Geigy Corporation, Ardsley, N.Y.

[21] Appl. No.: 879,474

[22] Filed: May 7, 1992

[51] Int. Cl.$^5$ .......................................... C07D 211/36
[52] U.S. Cl. .................................................... 546/242
[58] Field of Search ......................................... 542/242

[56] References Cited

U.S. PATENT DOCUMENTS

| | | | |
|---|---|---|---|
| 4,831,134 | 5/1989 | Winter et al. | 546/242 |
| 4,921,962 | 5/1990 | Galbo et al. | 546/184 |
| 5,004,770 | 4/1991 | Cortolano et al. | 524/99 |
| 5,021,481 | 6/1991 | Galbo et al. | 524/99 |
| 5,096,950 | 3/1992 | Galbo et al. | 524/99 |
| 5,112,890 | 5/1992 | Behrens et al. | 524/95 |

FOREIGN PATENT DOCUMENTS

| | | |
|---|---|---|
| 0309402 | 3/1989 | European Pat. Off. . |
| 0389419 | 9/1990 | European Pat. Off. . |

OTHER PUBLICATIONS

Sholle et al., Interaction of the Nitroxide Radical with Grignard Reagent pp. 761–763 No Date Available.
Inst. J. Chem., 1982, 35, 2013–24.
J. Org. Chem. vol. 40, No. 23, 1975.
Chemical Communications, 1968 pp. 891–892.
Polymer Journal, vol. 6, No. 5, pp. 445–447 (1974).
C.A. 101:91124n (1984).
C.A. 76:25049e (1972).
Journal of Physical Chemistry, vol. 77, No. 10 (1973) pp. 1218–1221.
Huyser, Free–Radical Chain Reactions (1970) p. 287.
Scott, Atmospheric Oxidation and Antioxidatants (1965) pp. 77–79.
Dixon & Norman, Electron Spin Resonance Studies of Oxidation (1963) pp. 3119–3127.
Briere et al., Chimie Organique Physique du Centre d'Etudes Nucleaires Chemia des Martyrs (1965) pp. 3273–3283.
Bruni et al., Radicalic Methylation Unexpected Formation of Sulfones & Sulfonamides p. 74 (1968).

*Primary Examiner*—C. Warren Ivy
*Assistant Examiner*—Raymond Covington
*Attorney, Agent, or Firm*—Luther A. R. Hall; Michele A. Kovaleski

[57] ABSTRACT

N-Methoxy derivatives of the sterically hindered amines 4-hydroxy-2,2,6,6-tetramethylpiperidine and 2,2,6,6-tetramethyl-4-piperidone are prepared from the corresponding N-oxyl hindered amine by combining hydrogen peroxide and a peroxide-decomposing transition metal salt in the presence of dimethyl sulfoxide.

7 Claims, No Drawings

PROCESS FOR PREPARING N-METHOXY DERIVATIVES OF 4-HYDROXY-2,2,6,6-TETRAMETHYLPIPERIDINE AND 2,2,6,6-TETRAMETHYL-4-PIPERIDONE

N-Methoxy derivatives of the sterically hindered amines 4-hydroxy-2,2,6,6-tetramethylpiperidine and 2,2,6,6-tetramethyl-4-piperidone are prepared by treating the corresponding N-oxyl hindered amine with hydrogen peroxide and a peroxide-decomposing transition metal salt in the presence of dimethyl sulfoxide.

N-Hydrocaxbyloxy derivatives of 2,2,6,6-tetramethylpiperidine are less basic than the corresponding N—H and N-alkyl compounds, and have recently been shown to be a particularly effective class of polymer stabilizers in substrates where the presence of the more basic N—H and N-alkyl hindered amines causes undesirable interactions. Examples of such applications include acid-catalyzed melamine crosslinked thermoset automotive coatings, poly(vinyl chloride), polyolefins containing flame-retardants, and polyolefins exposed to halogenated and/or sulfur containing compounds such as pesticides as taught in U.S. Pat. Nos. 5,004,770, 5,096,950 and 5,112,890.

The instant invention constitutes a process for the synthesis of N-methoxy derivatives of 4-hydroxy-2,2,6,6-tetramethylpiperidine and 2,2,6,6-tetramethyl-4-piperidone. These compounds are essential building blocks for the synthesis of more complex, commercially useful polymer stabilizers.

BACKGROUND OF THE INVENTION

When Fenton's reagent (hydrogen peroxide and a ferrous salt) is used in conjunction with a sulfoxide, α-cleavage of the sulfoxide occurs to produce carbon-centered radicals and a sulfinic acid.

The combination of $H_2O_2$-Fe(II) and dimethyl sulfoxide is one of the most efficient sources of the methyl radical (P. Bruni et al., *Proceedings of the 5th International Symposium on Organic Free Radicals*; H. Fischer, H. Heimgartner, Eds., Springer-Verlag: Berlin, 1988; p. 73).

The formation of 2-methoxy- 1,1,3,3-tetramethylisoindoline from the reaction of 2-oxyl-1,1,3,3-tetramethylisoindoline with ferrous sulfate, hydrogen peroxide, and dimethyl sulfoxide has been reported (E. Rizzardo et al., *Aust. J. Chem.* 1982, 35, 2013).

DETAILED DISCLOSURE

N-Methoxy derivatives of the sterically hindered 4-hydroxy-2,2,6,6-tetramethylpiperidine and 2,2,6,6-tetramethyl-4-piperidone are prepared from the corresponding N-oxyl hindered amine by combining hydrogen peroxide and a peroxide-decomposing transition metal salt in the presence of dimethyl sulfoxide as shown in equation (1)

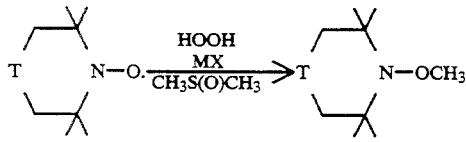

wherein

T is —C(O)— or —CH(OH)—, and
MX is a peroxide-decomposing transition metal salt.

Preferably, the transition metal salt is an iron(II) or iron(III) salt, but other metals such as titanium (III), copper(I) and copper (II) also are effective albeit with lower yields of product.

The instant invention is to a process for preparing the 1-methoxy-4-hydroxy-2,2,6,6-tetramethylpiperidine or 1-methoxy-2,2,6,6-tetramethyl-4-piperidone from the corresponding N-oxyl hindered amine by combining hydrogen peroxide and a peroxide-decomposing metal Fe(II), Fe(III), Ti(III), Cu(I) or Cu(II) salt in the presence of dimethyl sulfoxide which comprises adding a 1-10 molar equivalent (based on N-oxyl hindered amine) of 10-70% aqueous hydrogen peroxide to a mixture of N-oxyl hindered amine, a 1-10 molar equivalent of the Fe(II), Fe(III), Ti(III), Cu(I) or Cu(II) salt and a 1-500 molar equivalent of dimethyl sulfoxide at a temperature between −20° C. and 80° C.

The concentration of hydrogen peroxide and the rate of hydrogen peroxide addition can be adjusted to control the temperature of the reaction.

The sulfoxide functions as both a reagent and reaction solvent.

A co-solvent, such as tert-butyl alcohol or acetone, which will not interfere with the overall reaction, may be used. Water is an excellent co-solvent for the reaction. The addition of a strong mineral acid to the reaction mixture has no apparent effect on the yield. The reaction does not require an inert atmosphere.

Several variations in experimental procedure are possible. For example, an aqueous solution of the metal salt can be added to a mixture of the hydrogen peroxide, dimethyl sulfoxide, and N-oxyl substituted hindered amine. Another variation involves simultaneous addition of the metal salt and peroxide solutions to a mixture of the sulfoxide and N-oxyl amine at a relative rate which is adjusted to maintain a sufficient excess of either metal salt or peroxide.

After the reagents have been brought into contact, the reaction mixture is further stirred until the internal temperature no longer increases. An additional period of stirring has no apparent deleterious effect upon yield.

MX is ferric sulfate, titanium (III) chloride, copper(I) chloride, copper(II) sulfate or more preferably, a salt of $Fe^{++}$, such as ferrous chloride, ammonium iron(II) sulfate hexahydrate, iron(II) gluconate, iron(II) oxalate dihydrate, ferrous lactate dihydrate, or most preferably, ferrous sulfate heptahydrate.

The preferred reaction process involves adding 1-3 molar equivalent (based on N-oxyl hindered mine) of 20-50% hydrogen peroxide to a mixture of N-oxyl hindered amine, 1-2 molar equivalent of metal salt, and 10-100 molar equivalent of dimethyl sulfoxide at a temperature between −10° C. and 60° C. The most preferred process involves adding 1.2-2.5 molar equivalent (based on N-oxyl hindered amine) of 20-50% hydrogen peroxide to a mixture of N-oxyl hindered amine, 1-1.2 molar equivalent of ferrous sulfate heptahydrate, and 20-60 molar equivalent of dimethyl sulfoxide at a temperature between 10° C. and 40° C.

The instant process provides a superior method for the preparation of N-methoxy derivatives of the simple, commercially important hindered amines 2,2,6,6-tetramethyl-4-piperidone (triacetoneamine) and 4-hydroxy-2,2,6,6-tetramethylpiperidine (TMHP). Triacetoneamine and TMHP are essential building blocks for the synthesis of more complex commercial polymer stabilizers based on 2,2,6,6-tetramethylpiperidine. The elaboration of triacetoneamine and TMHP into more complex molecules involves reaction of the 4-oxo and 4-hydroxy groups. For example, triacetoneamine is reacted with diols to form ketals and with primary amines under reducing conditions to form secondary amine derivatives. The secondary amines may be subsequently reacted with carbonyl compounds or chlorotriazines. TMHP is converted into carboxylic acid ester derivatives by transesterification with methyl and ethyl esters of carboxylic acids.

The advantages of using N-hydrocarbyloxy derivatives of 2,2,6,6-tetramethylpiperidine hindered amines as polymer stabilizers are described above. The most effective general synthesis of N-hydrocarbyloxy hindered amine derivatives involves heating a hydrocarbon solution of the hindered amine or its N-oxyl derivative with tert-butyl hydroperoxide and a metal oxide catalyst as taught in U.S. Pat. No. 4,921,962. However, the use of this process to synthesize N-methoxy hindered amine derivatives is hampered by the low boiling point of methane (−161° C.).

Published methods for the synthesis of 1-methoxy-2,2,6,6-tetramethylpiperidine generally result in poor yields, and none of the chemistry is compatible with the functionality at C-4 in triacetoneamine and TMHP. For example, reaction of 1-oxyl-2,2,6,6-tetramethylpiperidine (TEMPO) with n-butyllithium and dimethyl sulfate or with sodium metal and methyl iodide results in 30–40% yields of 1-methoxy-2,2,6,6-tetramethylpipefidine (G. M. Whitesides and T. L. Newirth, *J. Org. Chem.* 1975, 40, 3448). A 75% yield of 1-methoxy-2,2,6,6-tetramethylpipefidine was reported when TEMPO was treated with methylmagnesium iodide (V. D. Sholle et al., *Dokl. Akad. Nauk SSSR* 1971, 200, 137), but the reaction of N-oxyl triacetoneamine or TMHP with a Grignard reagent is not feasible.

N-Methoxy hindered amine derivatives can be prepared by the reaction of N-oxyl hindered amines with methyl radicals generated by the thermal decomposition of di-tert-butyl peroxide at 120°–150° C. in an inert solvent such as chlorobenzene as taught in U.S. Pat. No. 5,021,481 and copending applications Ser. Nos. 480,173 and 749,470. The methyl radicals are formed from the β-scission of tert-butoxy radicals. This method of preparation gives significantly lower yields from both N-oxyl triacetoneamine and TMHP compared with yields obtained from the OH-protected 4-benzoyloxy-1-oxyl-2,2,6,6-tetramethylpiperidine. The instant process can be efficiently carried out at lower temperatures (10° C.–40° C.) and with shorter reaction times compared to the much higher temperatures and longer reaction times required for the efficient decomposition of di-tert-butyl peroxide (t₁₇₈ =6.4 hours. at 130° C.; E. S. Huyser, *Free-Radical Chain Reactions*; Wiley-Interscience: New York, 1970; p 287).

Rizzardo has reported that 2-methoxy-1,1,3,3-tetramethylisoindoline was synthesized in 77% yield, prior to recrystallization, by reacting 2-oxyl-1,1,3,3-tetramethylisoindoline with hydrogen peroxide, ferrous sulfate, and dimethyl sulfoxide under an argon atmosphere (E. Rizzardo et al., *Aust. J. Chem.* 1982, 35, 2013). There are no activated hydrogen atoms in this particular N-oxyl precursor. The conversion of N-oxyl triacetoneamine and TMHP to their N-methoxy derivatives using hydrogen peroxide, ferrous sulfate, and dimethyl sulfoxide as described in the instant process would be expected to be adversely affected by the presence of the ketone and alcohol functional groups. It is well known that alcohols and ketones increase the susceptibility of nearby hydrogen atoms toward abstraction by free radicals. For example, Scott discusses the preferential abstraction of hydrogen atoms α to carbonyl groups by methyl radicals (G. Scott, *Atmospheric Oxidation and Antioxidants*; Elsevier Publishing Company: New York, 1965; pp 78–79.). An investigation of the abstraction of hydrogen atoms from alcohols by methyl radicals (A. A. Herod, *Chemical Communications* 1968, 891) showed a preference for radical attack at the α-hydrogen position. Results from the reaction of alcohols with hydroxy radicals are consistent with preferential α-hydrogen abstraction (K. -D. Asmus et al., *J. Phys. Chem.* 1973, 77, 1218; W. T. Dixon and J. Norman, *J. Chem. Soc.* 1963, 3119).

The references cited would cause one to anticipate a significantly lower yield of N-methoxy product from the exposure of N-oxyl triacetoneamine and N-oxyl TMHP to the hydroxy and methyl radicals present in the hydrogen peroxide/ferrous sulfate/dimethyl sulfoxide system. The 80% isolated yields of N-methoxy triacetoneamine and N-methoxy TMHP obtained by the instant process are therefore quite unexpected.

A major advantage of the instant process over the procedure reported by Rizzardo et al. is that the instant process does not require an inert atmosphere where that of Rizzardo does.

The N-oxyl derivatives of 4-hydroxy-2,2,6,6-tetramethylpiperidine and 2,2,6,6-tetramethyl-4-piperidone are known compounds and may be prepared according to the method of Briere (R. Briere et al., *Bull. Soc. Chim. Fr.* 1965, 3273).

The substitution of cumyl hydroperoxide or tert-butyl hydroperoxide for hydrogen peroxide or of iron-(III) sulfate, titanium (III) chloride, copper(I) chloride or copper(II) sulfate for ferrous sulfate results in significantly reduced yields of product.

When di-n-butyl sulfoxide or diphenyl sulfoxide is used in place of dimethyl sulfoxide, low yields, respectively, of the N-n-butoxy and N-phenoxy substituted hindered amine derivatives are obtained. The use of methyl phenyl sulfoxide gives a mixture of N-methoxy and N-phenoxy substituted hindered amine derivatives.

The following examples are presented for the purpose of illustration only and are not to be construed to limit the nature of scope of the instant invention in any manner whatsoever.

EXAMPLE 1

1-Methoxy-2,2,6,6-tetramethyl-4-piperidone

A solution of 9.5 g (84 mmol) of 30% aqueous hydrogen peroxide is added dropwise, under nitrogen, over a 90-minute period to a mixture of 10.0 g (58.7 mmol) of 1-oxyl-2,2,6,6-tetramethyl-4-piperidone, 17.2 g (61.9 mmol) of ferrous sulfate heptahydrate, and 200 ml of dimethyl sulfoxide which is initially at a temperature of 25° C. The reaction temperature reaches 36° C. during the addition. After the peroxide is all added, the reaction mixture is stirred for two hours. During this time, the temperature falls to 25° C. The reaction mixture is cooled to 15° C. and diluted with water (100 ml). A solution of 8.6 g of sodium hydroxide in 85 ml of water is added to make the reaction mixture alkaline. The mixture is then extracted with methylene chloride (250 ml, then 2×150 ml). Water (200 ml) is added to help separate the layers. The organic layers are combined, dried over anhydrous magnesium sulfate, and concentrated under reduced pressure to obtain 50 g of a light green liquid. Purification by flash chromatography on silica gel (50:1 hexane/ethyl acetate, then 20:1 hexane/ethyl acetate) affords 8.6 g (79% yield) of the title compound as a white solid, mp 35–38° C.

Anal. calcd. for $C_{10}H_{19}NO_2$: C 64.8, H 10.3, N 7.6. Found: C 64.8, H 10.4, N 7.5.

EXAMPLE 2

1-Methoxy-4-hydroxy-2,2,6,6-tetramethylpiperidine

A solution of 9.2 g (81 mmol) of 30% aqueous hydrogen peroxide is added dropwise, under nitrogen, over a 75-minute period to a mixture of 10.0 g (58.1 mmol) of 4-hydroxy-1-oxyl-2,2,6,6-tetramethylpiperidine, 17.8 g (64.0 mmol) of ferrous sulfate heptahydrate, and 200 ml of dimethyl sulfoxide which is initially at a temperature of 25° C. The reaction temperature reaches 39° C. during the addition. After the peroxide is all added, the reaction mixture is stirred for 1.5 hours. During this time, the temperature falls to 26° C. The reaction mixture is cooled to 15° C. and diluted with water (150 ml). A solution of 7.5 g of sodium hydroxide in 70 ml of water is added to make the reaction mixture alkaline. The mixture is then extracted with methylene chloride (200 ml, then 2×150 ml). The organic layers are combined, dried over anhydrous magnesium sulfate, and concentrated under reduced pressure to obtain 53 g of a yellow liquid. Purification by flash chromatography on silica gel (10:1 hexane/ethyl acetate, then 5:1 hexane/ethyl acetate) affords 8.5 g (78% yield) of the title compound as a white solid, mp 92°–93° C.

Anal. calcd. for $C_{10}H_{21}NO_2$: C 64.1, H 11.3, N 7.5. Found: C 64.1, H 11.1, N 7.4.

Example 3 shows that the instant process does not need to be run in an inert atmosphere:

EXAMPLE 3

1-Methoxy-4-hydroxy-2,2,6,6-tetramethylpiperidine

A solution of 8.6 g (76 mmol) of 30% aqueous hydrogen peroxide is added dropwise, under nitrogen, over a 35-minute period to a mixture of 10.0 g (58.1 mmol) of 4-hydroxy-1-oxyl-2,2,6,6-tetramethylpiperidine, 17.8 g (64.0 mmol) of ferrous sulfate heptahydrate, and 200 ml of dimethyl sulfoxide which is initially at 25° C. A water bath is used to keep the reaction temperature from exceeding 33° C. during the peroxide addition. The reaction mixture is then stirred for 25 minutes and partitioned between methylene chloride (200 ml) and water (100 ml). The aqueous layer is extracted with methylene chloride (100 ml). The combined organic layers are dried over anhydrous magnesium sulfate and concentrated at reduced pressure. The crude product is purified by flash chromatography on silica gel (10:1 heptane/ethyl acetate, then 4:1 heptane/ethyl acetate) to afford 8.6 g (79% yield) of the title compound.

When the above experiment is carried out in the presence of air and in the absence of an inert atmosphere, the yield of the title compound is 8.8 g (81% yield). Clearly the presence of air does not adversely affect the instant process.

Examples 4–5 demonstrate the effect of temperature on the reaction:

EXAMPLE 4

1-Methoxy-4-hydroxy-2,2,6,6-tetramethylpiperidine

A solution of 9.1 g (80 mmol) of 30% aqueous hydrogen peroxide is added dropwise, under nitrogen, over a 30-minute period to a mixture of 10.0 g (58.1 mmol) of 4-hydroxy-1-oxyl-2,2,6,6-tetramethylpiperidine, 17.8 g (64.0 mmol) of ferrous sulfate heptahydrate, and 100 ml of dimethyl sulfoxide which is initially at 23° C. The reaction temperature reaches 65° C. during the addition. After the peroxide is all added, the reaction mixture is stirred for 30 minutes. During this time, the temperature falls to 35° C. The reaction mixture is partitioned between methylene chloride (150 ml) and water (100 ml). The organic layer is dried over anhydrous magnesium sulfate and concentrated at reduced pressure to obtain a yellow liquid. Purification by flash chromatography on silica gel (10:1 heptane/ethyl acetate, then 4:1 heptane/ethyl acetate) affords 6.5 g (60% yield) of the title compound.

EXAMPLE 5

1-Methoxy-4-hydroxy-2,2,6,6-tetramethylpiperidine

The procedure of Example 4 is repeated, except that the initial temperature is 4° C. and the hydrogen peroxide is added over 90 minutes. An ice-water bath is used to keep the reaction temperature at 5°–10° C. during the peroxide addition. The cooling bath is removed 5 minutes after the addition is complete, and the reaction mixture is stirred for 1 hour. The temperature gradually reaches 20° C. After extraction with methylene chloride and purification by chromatography, the yield of the title compound is 7.8 g (72% yield).

The effect of temperature on yield is summarized in Table 1 below.

TABLE 1

| Yield of N-Methoxy TMHP vs. Reaction Temperature* | | |
|---|---|---|
| Example | Temperature °C. | Yield |
| 3 | 25–33° | 79% |
| 4 | 23–65° | 60% |
| 5 | 5–10° | 81% |

*1.3–1.4 equiv. 30% $H_2O_2$ added to 10.0 g N-oxyl TMHP, 1.1 equiv. $FeSO_4$, and 100–200 ml DMSO over 30–90 min.

Example 6 demonstrates the effect of increasing the amount of hydrogen peroxide.

EXAMPLE 6

1-Methoxy-4-hydroxy-2,2,6,6-tetramethylpiperidine

The procedure of Example 3 is repeated with 14.5 g (128 mmol) of 30% hydrogen peroxide to afford 8.8 g (81% yield) of the title compound. The effect of changing the amount of hydrogen peroxide is summarized in Table 2 below.

TABLE 2

| Yield of N-methoxy TMHP vs. Hydrogen Peroxide Used* | | |
|---|---|---|
| Example | Equiv. $H_2O_2$ | Yield |
| 3 | 1.3 | 79% |
| 6 | 2.2 | 81% |

*30% $H_2O_2$ added to 10.0 g N-oxyl TMHP, 1.1 equiv. $FeSO_4$, and 200 ml DMSO over 30–60 min at 20–33° C.

Examples 7 and 8 demonstrate the effect of changing the amount of ferrous sulfate.

EXAMPLE 7

1-Methoxy-4-hydroxy-2,2,6,6-tetramethylpiperidine

The procedure of Example 3 is repeated with 8.1 g (29.1 mmol) of ferrous sulfate heptahydrate, 8.8 g (78 mmol) of 30% hydrogen peroxide, and a peroxide addition time of 15 minutes to afford 5.1 g (47% yield) of the title compound. A total of 2.4 g or 24% of unreacted 4-hydroxy-1-oxyl-2,2,6,6-tetramethylpiperidine starting material is recovered from the reaction mixture.

EXAMPLE 8

1-Methoxy-4-hydroxy-2,2,6,6-tetramethylpiperidine

The procedure of Example 3 is repeated with 24.4 g (87.8 mmol) of ferrous sulfate heptahydrate, 14.0 g (124 mmol) of 30% hydrogen peroxide, and a peroxide addition time of 15 minutes to afford 8.7 g (80% yield) of the title compound.

The effect of changing the amount of ferrous sulfate heptahydrate is summarized in Table 3 below.

TABLE 3

Yield of N-methoxy TMHP vs. Ferrous Sulfate Used*

| Example | Equiv. FeSO$_4$ | Yield |
|---|---|---|
| 7 | 0.5 | 47% |
| 3 | 1.1 | 79% |
| 8** | 1.5 | 80% |

*1.3 equiv. 30% H$_2$O$_2$ added to 10.0 g N-oxyl TMHP, FeSO$_4$, and 200 ml DMSO over 15-35 min at 20-33°.
**2.1 equiv. H$_2$O$_2$ used in this example.

Example 9 demonstrates the effect of the addition of sulfuric acid to the reaction mixture.

EXAMPLE 9

1-Methoxy-4-hydroxy-2,2,6,6-tetramethylpiperidine

The procedure of Example 3 is repeated, except that a solution of 6.3 g (62 mmol) of 96% sulfuric acid in 35 ml of water is added to the reaction mixture prior to the addition of hydrogen peroxide. Solid sodium carbonate (7 g) is added to the reaction mixture prior to extraction with methylene chloride. The yield of the title compound is 8.0 g (73% yield).

The effect of acid on the reaction is summarized in Table 4 below.

TABLE 4

Effect of Acid on Yield of N-methoxy TMHP*

| Example | Equiv. H$_2$SO$_4$ | Yield |
|---|---|---|
| 3 | none | 79% |
| 9 | 1.1 | 73% |

*1.3 equiv. 30% H$_2$O$_2$ added to 10.0 g N-oxyl TMHP, 1.1 equiv. FeSO$_4$, conc. H$_2$SO$_4$, and 200 ml DMSO over 35-70 min at 25-33° C.

Examples 10 and 11 demonstrate the effect of hydrogen peroxide addition time on yield.

EXAMPLE 10

1-Methoxy-4-hydroxy-2,2,6,6-tetramethylpipefidine

The procedure of Example 3 is repeated, except that hydrogen peroxide is added over 55 minutes and the reaction mixture is stirred for 2 hours after the addition is complete. The yield of the title compound is 8.5 g (78% yield).

EXAMPLE 11

1-Methoxy-4-hydroxy-2,2,6,6-tetramethylpipefidine

The procedure of Example 3 is repeated, except that hydrogen peroxide is added over 10 minutes while the reaction temperature is kept at 20°-33° C. by use of a cooling bath. The mixture is stirred for 20 minutes after the peroxide addition is complete. The yield of the title compound is 8.7 g (80% yield).

The effect of reaction time on yield is summarized in Table 5 below.

TABLE 5

Yield of N-methoxy TMHP vs. Peroxide Addition Time*

| Example | Addition Time | Yield |
|---|---|---|
| 11 | 10 min | 80% |
| 3 | 35 min | 79% |
| 10 | 55 min | 78% |
| 2 | 75 min | 78% |
| 5** | 90 min | 72% |

*1.3-1.4 equiv. 30% H$_2$O$_2$ added to 10.0 g N-oxyl TMHP, 1.1 equiv. FeSO$_4$, and 200 ml DMSO at 20-33° C.
**1.4 equiv. 30% H$_2$O$_2$ added to 10.0 g N-oxyl TMHP, 1.1 equiv. FeSO$_4$, and 100 ml DMSO at 4-10° C.

Examples 12-15 demonstrate the effect of dimethyl sulfoxide on yield.

EXAMPLE 12

1-Methoxy-4-hydroxy-2,2,6,6-tetramethylpiperidine

The procedure of Example 3 is repeated, except that the 200 ml of dimethyl sulfoxide is replaced by a mixture of 4 ml (59 mmol) of dimethyl sulfoxide and 96 ml of water. The yield of the title compound is 0.4 g (4% yield).

EXAMPLE 13

1-Methoxy-4-hydroxy-2,2,6,6-tetramethylpiperidine

The procedure of Example 3 is repeated, except that the 200 ml of dimethyl sulfoxide is replaced by a mixture of 21 ml (0.30 mol) of dimethyl sulfoxide and 79 ml of water. The yield of the title compound is 2.2 g (20% yield).

EXAMPLE 14

1-Methoxy-4-hydroxy-2,2,6,6-tetramethylpiperidine

The procedure of Example 3 is repeated, except that the 200 ml of dimethyl sulfoxide is replaced by a mixture of 42 ml (0.59 mmol) of dimethyl sulfoxide and 58 ml of water. The yield of the title compound is 4.4 g (40% yield).

EXAMPLE 15

1-Methoxy-4-hydroxy-2,2,6,6-tetramethylpiperidine

The procedure of Example 3 is repeated, except that the amount of dimethyl sulfoxide is increased to 400 ml. The yield of the title compound is 7.8 g (72% yield).

The effect of the amount of dimethyl sulfoxide on yield is summarized in Table 6 below.

TABLE 6

Yield of N-methoxy TMHP vs. Dimethyl Sulfoxide Used*

| Example | Equiv. DMSO | Yield |
|---|---|---|
| 12** | 1 | 4% |
| 13** | 5 | 20% |
| 14** | 10 | 40% |
| 5 | 24 | 72% |
| 3 | 48 | 79% |
| 15 | 97 | 72% |

*1.3-1.4 equiv. 30% H$_2$O$_2$ added to 10.0 g N-oxyl TMHP, 1.1 equiv. FeSO$_4$, and DMSO over 25-105 min at 4-33° C.
**Water is added to DMSO to bring total volume of solvent to 100 ml.

EXAMPLE 16 demonstrates the effect of simultaneous addition of hydrogen peroxide and ferrous sulfate to a mixture of N-oxyl compound and dimethyl sulfoxide.

EXAMPLE 16

1-Methoxy-4-hydroxy-2,2,6,6-tetramethylpiperidine

A solution of 17.9 g (64.4 mmol) of ferrous sulfate heptahydrate in 80 ml of water and a solution of 9.7 g (86 mmol) of 30% aqueous hydrogen peroxide are simultaneously added, under nitrogen, over a 90-minute interval to a mixture of 10.0 g (58.1 mmol) of 4-hydroxy-1-oxyl-2,2,6,6-tetramethylpiperidine and 100 ml of dimethyl sulfoxide which is initially at 23° C. The temperature increases to 29° C. during the peroxide addition. After the addition is complete, the reaction mixture is stirred for two hours. The mixture is extracted with methylene chloride (200 ml, then 100 ml), and the crude product is purified by flash chromatography on silica gel (10:1 heptane/ethyl acetate, then 5:1 heptane/ethyl acetate) to afford 6.9 g (63% yield) of the title compound.

Examples 17 and 18 demonstrate the effect of the addition of aqueous ferrous sulfate to a mixture of N-oxyl compound, hydrogen peroxide, and dimethyl sulfoxide.

EXAMPLE 17

1-Methoxy-4-hydroxy-2,2,6,6-tetramethylpiperidine

A solution of 17.8 g (64.0 mmol) of ferrous sulfate heptahydrate in 80 ml of water is added dropwise, under nitrogen, over a 100-minute interval to a mixture of 10.0 g (58.1 mmol) of 4-hydroxy-1-oxyl-2,2,6,6-tetramethylpiperidine, 8.3 g (73 mmol) of 30% aqueous hydrogen peroxide, and 100 ml of dimethyl sulfoxide. As the ferrous sulfate solution is added, the reaction temperature rapidly increases from 27° C. to 43° C. A cooling bath is used to regulate the temperature, which reaches 53° C. and then begins to decrease. The reaction mixture is stirred for 30 minutes after the ferrous sulfate solution is added, and then extracted with methylene chloride (3×100 ml). The crude product is purified by flash chromatography on silica gel (10:1 heptane/ethyl acetate, then 4:1 heptane/ethyl acetate) to afford 2.7 g (25% yield) of the title compound.

EXAMPLE 18

1-Methoxy-4-hydroxy-2,2,6,6-tetramethylpiperidine

A solution of 17.8 g (64.0 mmol) of ferrous sulfate heptahydrate in 100 ml of water is added dropwise, under nitrogen, over an 8-minute interval to a mixture of 10.0 g (58.1 mmol) of 4-hydroxy-1-oxyl-2,2,6,6-tetramethylpiperidine, 14.5 g (128 mmol) of 30% aqueous hydrogen peroxide, and 200 ml of dimethyl sulfoxide. As the ferrous sulfate solution is added, an ice-water bath is used to keep the reaction temperature at 20° C.–40° C. After the addition is complete, the mixture is stirred for 15 minutes at ambient temperature and then extracted with methylene chloride (200 ml, then 100 ml). Purification of the crude product by flash chromatography on silica gel (10:1 heptane/ethyl acetate, then 4:1 heptane/ethyl acetate) affords 5.7 g (52% yield) of the title compound.

Example 19 demonstrates the effect of replacing ferrous sulfate with other metal salts.

EXAMPLE 19

1-Methoxy-4-hydroxy-2,2,6,6-tetramethylpiperidine

A solution of 9.0 g (79 mmol) of 30% aqueous hydrogen peroxide is added dropwise, under nitrogen, over a 10-minute period to a mixture of 10.0 g (58.1 mmol) of 4-hydroxy-1-oxyl-2,2,6,6-tetramethylpiperidine, 31.4 g (64.1 mmol) of ferric sulfate pentahydrate, and 200 ml of dimethyl sulfoxide at a temperature of 20° C. No temperature change is observed as the hydrogen peroxide solution is added. After the addition is complete, the reaction mixture is stirred for 10 minutes. Water (50 ml) is added, and the temperature increases to 45° C. The mixture is diluted with methylene chloride (200 ml) and water (50 ml), and the aqueous layer is extracted with methylene chloride (2×100 ml). The organic layers are concentrated at reduced pressure, and the crude product is purified by flash chromatography on silica gel (4:1 heptane/ethyl acetate) to afford 1.25 g (11% yield) of the title compound, mp 93°–94° C.

The above procedure is repeated using 15.9 g (63.7 mmol) of copper(II) sulfate pentahydrate in place of ferric sulfate pentahydrate. The hydrogen peroxide is added over a 25 minute interval, and the reaction temperature increases from 22° C. to 55° C. during the addition. The yield of the title compound is 1.6 g (15% yield).

When copper(II) sulfate pentahydrate is replaced with 6.3 g (63.6 mmol) of cuprous chloride, 300 mg of the title compound is obtained.

A solution of 7.2 g (5.6 mmol) of 12% titanium(III) chloride in hydrochloric acid is added dropwise under nitrogen over a 15 minute period to a mixture of 1.0 g (5.8 mmol) of 4-hydroxy-1-oxyl-2,2,6,6-tetramethylpiperidine, 1.0 g (8.8 mmol) of hydrogen peroxide, and 15 ml of dimethyl sulfoxide at a temperature of 20° C. The reaction temperature increases to 30° C. during the addition. The mixture is stirred for 45 minutes after the peroxide addition is complete, and is then diluted with methylene chloride (50 ml). The aqueous layer is neutralized by the addition of a saturated aqueous solution of sodium carbonate, then extracted with methylene chloride (50 ml). The combined organic layers are concentrated under reduced pressure, and the crude product is purified by flash chromatography on silica gel (4:1, heptane:ethyl acetate) to afford 100 mg (10% yield) of the title compound.

Examples 20 and 21 illustrate the advantage of the instant process over the use of di-tert-butyl peroxide for the synthesis of 1-methoxy-2,2,6,6-tetramethyl-4-piperidone and 1-methoxy-4-hydroxy-2,2,6,6-tetramethylpiperidine.

Examples 20–22 illustrate that the yield of N-methoxy product obtained by reacting N-oxyl triacetoneamine and TMHP with methyl radicals resulting from the thermolysis of di-tert-butyl peroxide is significantly lower than the yield obtained when the less reactive 4-benzoyloxy derivative of N-oxyl TMHP is used.

EXAMPLE 20

1-Methoxy-2,2,6,6-tetramethyl-4-piperidone

A mixture of 10.0 g (58.7 mmol) of 1-oxyl-2,2,6,6-tetramethyl-4-piperidone, 8.6 g (59 mmol) of di-tert-butyl peroxide, and 80 ml of o-dichlorobenzene is heated at 145° C. (internal temperature) under nitrogen for 2.5 hours. Volatile materials are collected in a Dean-Stark trap. The reaction mixture is cooled to room temperature and poured onto a column of silica gel. The column is first eluted with heptane to remove o-dichlorobenzene, and then eluted with 10:1 heptane/ethyl acetate to obtain 8 g of a three-component mixture. The mixture is distilled under vacuum, and three fractions are collected. TLC shows that all of the fractions contain the title compound and two contaminants. The three impure fractions are combined to obtain 4.8 g (44% yield, if pure) of a yellow liquid. This result is compared with the 79% yield of the title compound obtained as a white solid, mp 35°–38° C., according to the procedure of Example 1.

EXAMPLE 21

1-Methoxy-4-hydroxy-2,2,6,6-tetramethylpiperidine

A mixture of 10.0 g (58.1 mmol) of 4-hydroxy-1-oxyl-2,2,6,6-tetramethylpiperidine, 8.6 g (59 mmol) of di-tert-butyl peroxide, and 80 ml of o-dichlorobenzene is heated at 145°–150° C. (internal temperature) under nitrogen for 3.5 hours. Volatile materials are collected in a Dean-Stark trap. The reaction mixture is cooled to room temperature and poured onto a column of silica gel. The column is first eluted with heptane to remove o-dichlorobenzene, and then eluted with 10:1 heptane/ethyl acetate followed by 4:1 heptane/ethyl acetate to obtain 7.6 g of an orange solid. The crude reaction product is recrystallized twice from heptane to remove the impurity and afford 3.9 g (36% yield) of the title compound. This result is compared with the 78% yield of the title compound obtained according to the procedure of Example 2.

EXAMPLE 22

4-Benzoyloxy-1-methoxy-2,2,6,6-tetramethylpiperidine

A mixture of 40.1 g (145 mmol) of 4-benzoyloxy-1-oxyl-2,2,6,6-tetramethylpiperidine, 21.8 g (149 mmol) of di-tert-butyl peroxide, and 200 ml of o-dichlorobenzene is heated at 145° C. (internal temperature) under nitrogen for 1.75 hours. Volatile materials are collected in a Dean-Stark trap. The reaction mixture is cooled to room temperature and poured onto a column of silica gel. The column is first eluted with hexane to remove o-dichlorobenzene, and then eluted with 25:1 hexane/ethyl acetate to obtain 43 g of a yellow solid. Final purification by HPLC (Waters Prep 500A, 50:1 hexane/ethyl acetate) affords 33.9 g (80% yield) of the title compound.

Examples 1, 2, and 23 demonstrate that, in contrast to the prior art di-tert-butyl peroxide process, yields from the instant process are not adversely affected by the reactive 4-oxo and 4-hydroxy groups present in triacetoneamine and TMHP.

EXAMPLE 23

4-Benzoyloxy-1-methoxy-2,2,6,6-tetramethylpiperidine

A solution of 5.9 g (52 mmol) of 30% aqueous hydrogen peroxide is added dropwise, under nitrogen, over 90 minutes to a mixture of 10.0 g (36.2 mmol) of 4-benzoyloxy-1-oxyl-2,2,6,6-tetramethylpiperidine, 11.2 g (40.3 mmol) of ferrous sulfate heptahydrate, and 135 ml of dimethyl sulfoxide which is initially at 24° C. The reaction temperature increases to 37° C. as the peroxide is added. After the addition is complete, the reaction mixture is stirred for 1.75 hours at ambient temperature. The mixture is cooled in an ice-water bath and diluted with water (80 ml). A solution of 5 g of sodium hydroxide in 45 ml of water is added to make the reaction mixture basic. The mixture is extracted with methylene chloride (250 ml, then 2×150 ml), and the combined organic layers are concentrated at reduced pressure to obtain a light orange liquid. Purification of the crude product by flash chromatography on silica gel (20:1 heptane/ethyl acetate) affords 8.5 g (81% yield) of the title compound, a white solid, mp 67°–69° C.

Anal. Cald. for $C_{17}H_{25}NO_3$: C 70.1, H 8.6, N 4.8. Found: C 70.2, H 8.9, N 4.7.

What is claimed is:

1. A process for preparing 1-methoxy-4-hydroxy-2,2,6,6-tetramethylpiperidine or 1-methoxy-2,2,6,6-tetramethyl-4-piperidone from the corresponding N-oxyl hindered amine by combining hydrogen peroxide and a peroxide-decomposing metal Fe(II), Fe(III), Ti(III), Cu(I) or Cu(II) salt in the presence of dimethyl sulfoxide comprises adding a 1–10 molar equivalent (based on N-oxyl hindered amine) of 10–70% aqueous hydrogen peroxide to a mixture of N-oxyl hindered amine, a 1–10 molar equivalent of the Fe(II), Fe(III), Ti(III), Cu(I) or Cu(II) salt and a 1–500 molar equivalent of dimethyl sulfoxide at a temperature between −20° C. and 80° C.

2. A process according to claim 1 wherein a co-solvent selected from the group consisting of tert-butyl alcohol, acetone and water is also present.

3. A process according to claim 2 wherein water is present as a co-solvent.

4. A process according to claim 1 wherein the salt is ferric sulfate, titanium(III) chloride, copper(I) chloride, copper(II) sulfate, ferrous chloride, ammonium iron(II) sulfate hexahydrate, iron(II) gluconate, iron(II) oxalate dihydrate, ferrous lactate dihydrate or ferrous sulfate.

5. A process according to claim 4 wherein the salt is ferrous sulfate heptahydrate.

6. A process according to claim 1 which comprises adding a 1–3 molar equivalent (based on N-oxyl hindered amine) of 20–50% hydrogen peroxide to a mixture of N-oxyl hindered amine, a 1–2 molar equivalent of metal salt, and a 10–100 molar equivalent of dimethyl sulfoxide at a temperature between −10° C. and 60° C.

7. A process according to claim 1 which comprises adding a 1.2–2.5 molar equivalent (based on N-oxyl hindered mine) of 20–50% hydrogen peroxide to a mixture of N-oxyl hindered mine, a 1–1.2 molar equivalent of ferrous sulfate heptahydrate, and a 20–60 molar equivalent of dimethyl sulfoxide at a temperature between 10° C. and 40° C.

* * * * *